US00PP24124P2

(12) United States Plant Patent
Lannes

(10) Patent No.: US PP24,124 P2
(45) Date of Patent: Dec. 31, 2013

(54) ***MANDEVILLA* PLANT NAMED 'LANIDAHO'**

(50) Latin Name: *Mandevilla sanderi*
Varietal Denomination: Lanidaho

(75) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 106 days.

(21) Appl. No.: 13/374,920

(22) Filed: Jan. 23, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

(56) References Cited

PUBLICATIONS

Pluto Upov Plant Variety Database 2013/01, retrieved on Jun. 20, 2013, retrieved from the Internet at <http://www.upov.int/pluto/en/index.jsp> for Mandevilla 'Lanidaho', one page.*

* cited by examiner

*Primary Examiner* — June Hwu
(74) *Attorney, Agent, or Firm* — C. A. Whealy

(57) ABSTRACT

A new and distinct cultivar of *Mandevilla* plant named 'Lanidaho', characterized by its compact and bushy plant habit; moderately vigorous growth habit; glossy dark green-colored leaves; early flowering habit; and dark red-colored flowers.

2 Drawing Sheets

Botanical designation: *Mandevilla sanderi.*
Cultivar denomination: 'LANIDAHO'.

BACKGROUND OF THE INVENTION

The present invention relates to a new and distinct cultivar of *Mandevilla* plant, botanically known as *Mandevilla sanderi* and hereinafter referred to by the name 'Lanidaho'.

The new *Mandevilla* plant is a product of a planned breeding program conducted by the Inventor in Malause, France. The objective of the breeding program is to create new freely branching *Mandevilla* plants with dark red-colored flowers.

The new *Mandevilla* plant originated from a cross-pollination conducted by the Inventor in Malause, France on Mar. 2, 2007 of a proprietary selection of *Mandevilla sanderi* identified as code number 05-050-15, not patented, as the female, or seed parent with *Mandevilla sanderi* 'Dark', not patented, as the male, or pollen, parent. The new *Mandevilla* plant was discovered and selected by the Inventor as a single flowering plant from within the progeny of the stated cross-pollination in a controlled greenhouse environment in Malause, France in June, 2009.

Asexual reproduction of the new *Mandevilla* plant by cuttings in a controlled greenhouse environment in Malause, France, since May, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanidaho'. These characteristics in combination distinguish 'Lanidaho' as a new and distinct *Mandevilla* plant:

1. Compact and bushy plant habit.
2. Moderately vigorous growth habit.
3. Glossy dark green-colored leaves.
4. Early flowering habit.
5. Dark red-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* are more compact and have shorter internodes than plants of the female parent selection.
2. Plants of the new *Mandevilla* have larger leaves than plants of the female parent selection.
3. Plants of the new *Mandevilla* flower earlier than plants of the female parent selection.
4. Plants of the new *Mandevilla* have larger flowers than plants of the female parent selection.

Plants of the new *Mandevilla* can be compared to plants of the male parent, 'Dark'. Plants of the new *Mandevilla* differ primarily from plants of 'Dark' in the following characteristics:

1. Plants of the new *Mandevilla* are more compact and have shorter internodes than plants of 'Dark'.
2. Plants of the new *Mandevilla* are more freely branching than plants of 'Dark'.
3. Plants of the new *Mandevilla* flower earlier than plants of 'Dark'.
4. Plants of the new *Mandevilla* and 'Dark' differ in flower color as plants of 'Dark' have pink-colored flowers.
5. Plants of the new *Mandevilla* have larger flowers than plants of 'Dark'.

Plants of the new *Mandevilla* can also be compared to plants of selections of *Mandevilla sanderi* known to the Inventor, not patented. In side-by-side comparisons conducted in Malause, France, plants of the new *Mandevilla* differed from plants of selections of *Mandevilla sanderi* known to the Inventor in the following characteristics:

1. Plants of the new *Mandevilla* were more freely branching than plants of selections of *Mandevilla sanderi* known to the Inventor.
2. Plants of the new *Mandevilla* had smaller leaves than plants of selections of *Mandevilla sanderi* known to the Inventor.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanidaho' grown in a container.

The photograph on the second sheet is a close-up view of a typical flowering plant of 'Lanidaho'.

DETAILED BOTANICAL DESCRIPTION

The aforementioned photographs and following observations, measurements and values describe plants grown during the autumn in 10.5-cm containers in polyethylene-covered greenhouse in Malause, France and under cultural practices typical of *Mandevilla* commercial production. During the production of the plants, day temperatures ranged from 8° C. to 26° C. and night temperatures ranged from 3° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla sanderi* 'Lanidaho'.

Parentage:

*Female, or seed, parent*.—Proprietary selection of *Mandevilla sanderi* identified as code number 05-050-15, not patented.

*Male, or pollen, parent*.—*Mandevilla sanderi* 'Dark', not patented.

Propagation:

*Type*.—By vegetative cuttings.

*Time to initiate roots, summer*.—About two weeks at 23° C. to 25° C.

*Time to initiate roots, winter*.—About three weeks at 23° C. to 25° C.

*Time to produce a rooted young plant, summer*.—About five to six weeks at 23° C. to 25° C.

*Time to produce a rooted young plant, winter*.—About six to eight weeks at 23° C. to 25° C.

*Root description*.—Fibrous, fine; light yellowish white in color.

*Rooting habit*.—Freely branching; medium density.

Plant description:

*Plant and growth habit*.—Compact and bushy plant habit; upright and somewhat outwardly spreading; broad inverted triangle in shape; moderately vigorous growth habit.

*Plant height*.—About 25.9 cm.

*Plant diameter* (*spread*).—About 27.3 cm.

*Lateral branch description*.—Branching habit: Moderately freely branching habit with about four lateral branches developing per plant; pinching enhances lateral branch development. Length: About 11 cm. Diameter: About 2 mm. Internode length: About 1.9 cm. Strength: Strong. Texture: Smooth, glabrous. Color: Close to 144A to 144B; older stems, close to 199A.

Foliage description:

*Arrangement*.—Opposite, simple.

*Length*.—About 6.4 cm.

*Width*.—About 4.1 cm.

*Shape*.—Obovate.

*Apex*.—Abruptly bluntly acute.

*Base*.—Obtuse to truncate.

*Margin*.—Entire.

*Texture, upper and lower surfaces*.—Smooth, glabrous; glossy.

*Venation pattern*.—Pinnate, reticulate.

*Color*.—Developing leaves, upper surface: Darker than between 143A and 146A. Developing leaves, lower surface: Close to 146B tinged with close to N199A. Full expanded leaves, upper surface: Darker than between N137C and 147A; venation, close to 143A. Fully expanded leaves, lower surface: Between 138A and 146B; venation, close to 144D.

*Petiole length*.—About 1.2 cm.

*Petiole diameter*.—About 1.5 mm.

*Petiole texture, upper and lower surfaces*.—Smooth, glabrous.

*Petiole color, upper surface*.—Close to 144D tinged with close to 153D.

*Petiole color, lower surface*.—Close to 144D.

Flower description:

*Flower type and flowering habit*.—Single salverform flowers arranged in axillary racemes; flowers star-shaped and face upright and outwardly; about four flowers developing per inflorescence and about 24 flowers developing per plant.

*Natural flowering season*.—Early flowering habit with plants begin to flower about six weeks after planting; plants flower continuously from summer into the autumn in France.

*Flower longevity on the plant*.—About seven days; flowers not persistent.

*Fragrance*.—Very faint, pleasant.

*Flowers*.—Appearance: Flared trumpet, corolla fused and five-parted. Diameter: About 8.1 cm. Depth (length): About 7.2 cm. Tube length: About 5.5 cm.

*Flower buds*.—Length: About 5.2 cm. Diameter: About 9 mm. Shape: Narrowly obovate. Color: Close to 145C; towards the base, close to 144C.

*Corolla*.—Quantity and arrangement: Five petals arranged in a single whorl and fused at the base. Petal lobe length: About 4 cm. Petal lobe width: About 3.5 cm. Petal shape and appearance: Roughly spatulate; lower 57.5% of the petal is fused. Petal apex: Bluntly acute. Petal margin: Entire. Petal texture, upper and lower surfaces: Smooth, glabrous; slightly velvety. Throat texture: Smooth, glabrous. Tube texture: Smooth, glabrous. Color: Petal, when opening, upper surface: Between 46A and 53A, towards the base, close to 53A; throat, close to 26A, towards the base of the throat, close to N144D. Petal, when opening, lower surface: Between 53A and 187C; mid-vein, close to N155A, towards the base, close to 58A; tube, close to 145C, towards the base of the tube, close to 145A. Petal, fully opened, upper surface: Darker than 53A, towards the base, between 45B and 46B; throat, close to 34B, towards the base of the throat, close to 151D; with development, color becoming closer to between 46A and 53A. Petal, fully opened, lower surface: Close to 53A; mid-vein, close to N155A, towards the base, close to 54A; tube, close to 145A.

*Calyx*.—Quantity and arrangement: Five sepals arranged in a single whorl. Sepal length: About 1 cm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature, upper and lower surfaces: Close to 145B. Mature, upper and lower surfaces: Close to 145B.

*Peduncles*.—Length: About 5.9 cm. Diameter: About 2 mm. Texture: Smooth, glabrous. Strength: Flexible, but strong. Color: Close to 144A to 144B.

*Pedicels*.—Length: About 1.4 cm. Diameter: About 2 mm. Texture: Smooth, glabrous. Strength: Flexible, but strong. Color: Close to 145A.

*Reproductive organs*.—Stamens: Quantity and arrangement: Typically five; basifixed; anthers connivent. Filament length: About 1 mm. Anther shape: Ellipsoidal. Anther length: About 9 mm. Anther color: Close to 162B to 162C. Pollen amount: None observed. Pistils: Quantity: Typically one. Pistil length: About 2.6 cm. Style length: About 2.3 cm. Style color: Close to 150D. Stigma shape: Conical. Stigma color: Close to 146A to 146B. Ovary color: Close to 146B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lanidaho' as illustrated and described.

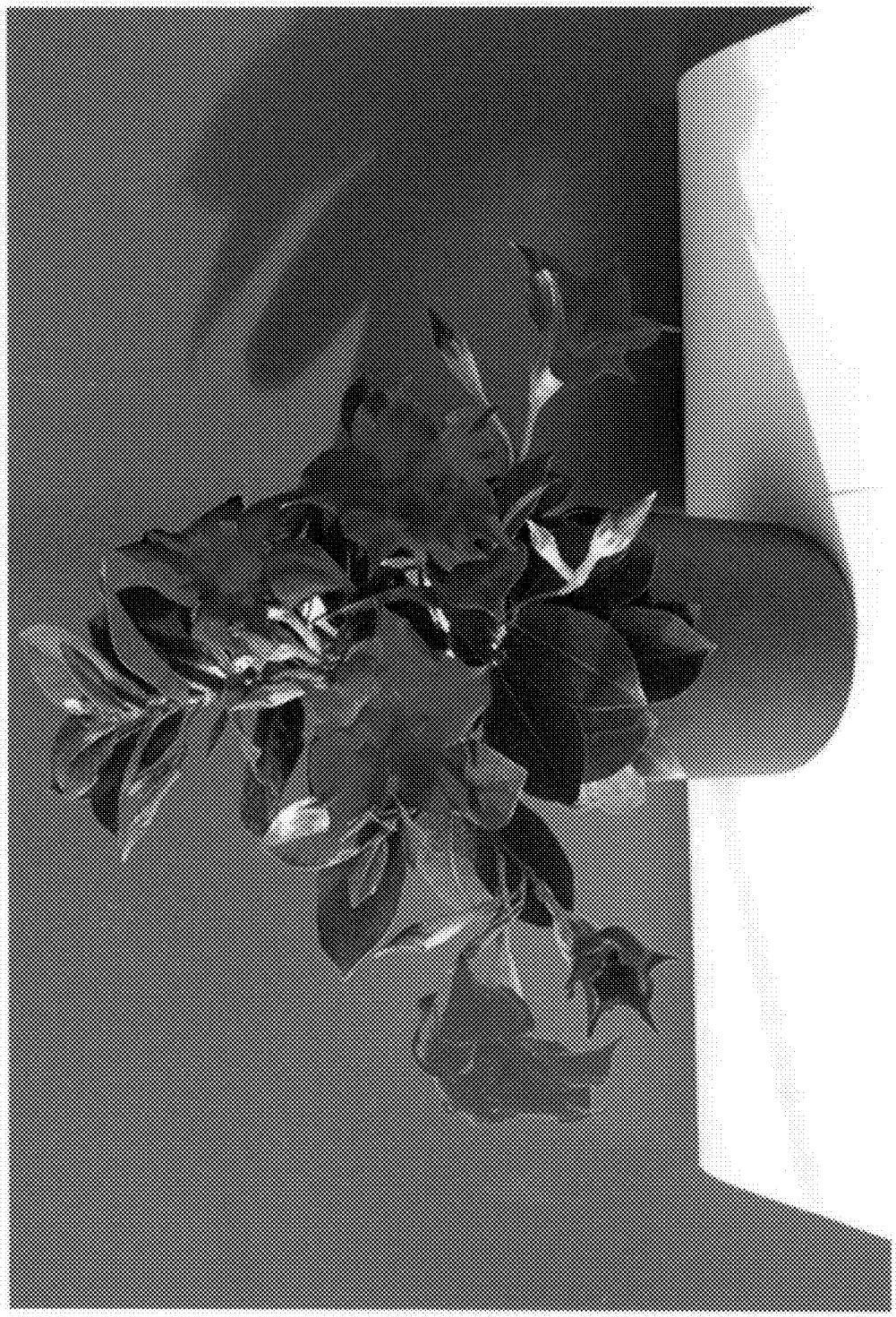

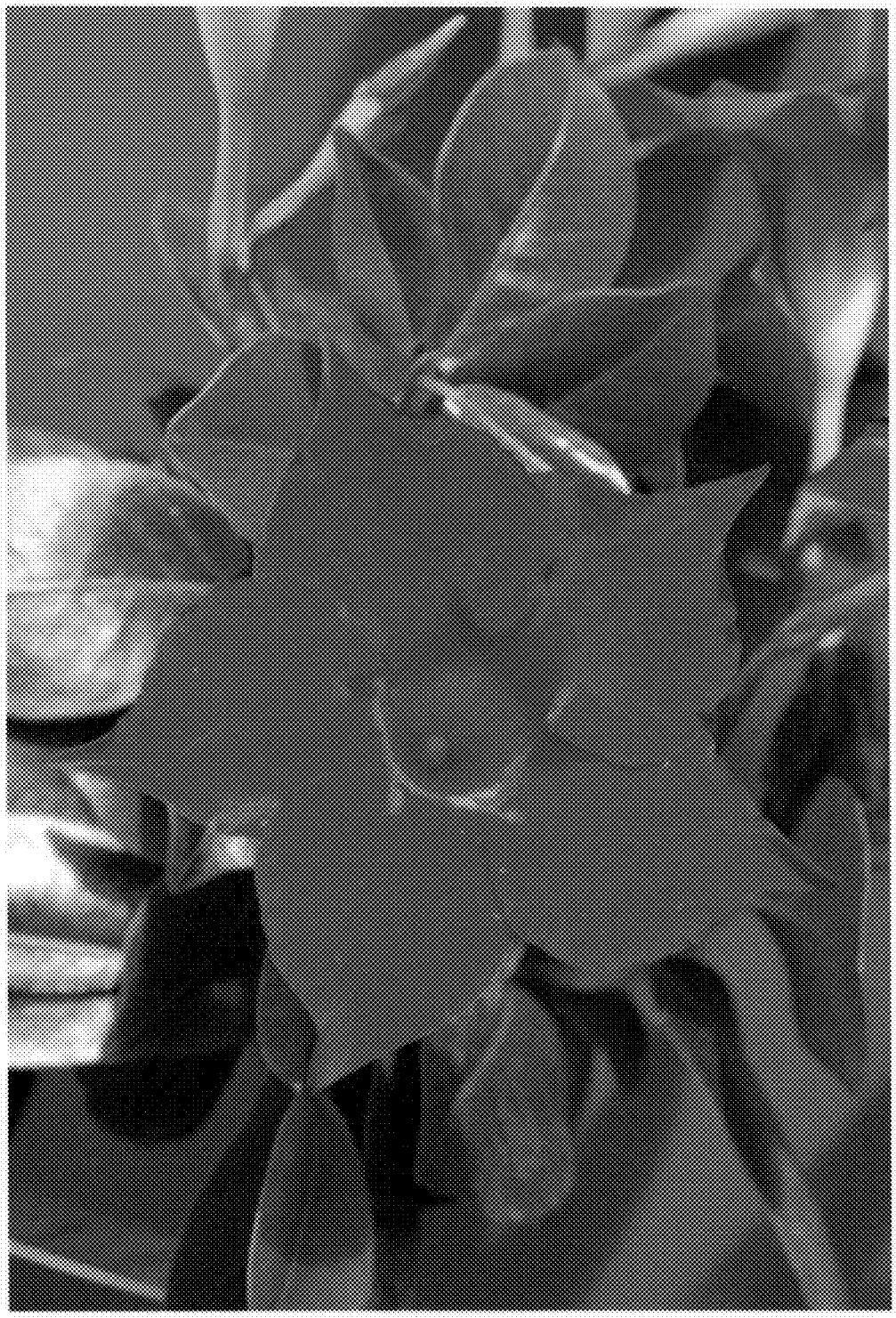

* * * * *